United States Patent
Vasta

(10) Patent No.: US 8,167,880 B2
(45) Date of Patent: May 1, 2012

(54) ADJUSTABLE FIXATION DEVICES INCORPORATING DRIVE SYSTEMS

(75) Inventor: Paul J. Vasta, McKinney, TX (US)

(73) Assignee: AMEI Technologies, Inc., Wilmington, DE (US)

( * ) Notice: Subject to any disclaimer, the term of this patent is extended or adjusted under 35 U.S.C. 154(b) by 917 days.

(21) Appl. No.: 12/047,677

(22) Filed: Mar. 13, 2008

(65) Prior Publication Data
US 2008/0312656 A1 Dec. 18, 2008

Related U.S. Application Data

(60) Provisional application No. 60/943,816, filed on Jun. 13, 2007.

(51) Int. Cl.
*A61B 17/00* (2006.01)
(52) U.S. Cl. .......................................................... 606/54
(58) Field of Classification Search ............... 606/53–59; 74/351, 496, 406, 424.83, 490.12, 89.18, 74/416, 425, 490.09
See application file for complete search history.

(56) References Cited

U.S. PATENT DOCUMENTS

| | | | |
|---|---|---|---|
| 3,631,582 A * | 1/1972 | Lucas et al. ................. | 29/419.1 |
| 4,498,889 A | 2/1985 | Stevens et al. | |
| 5,334,202 A * | 8/1994 | Carter ............................. | 606/58 |
| 6,129,727 A * | 10/2000 | Austin et al. .................... | 606/56 |
| 6,171,309 B1 * | 1/2001 | Huebner ......................... | 606/57 |
| 2002/0010465 A1 * | 1/2002 | Koo et al. ....................... | 606/57 |
| 2003/0036462 A1 * | 2/2003 | Ravikumar et al. ............ | 482/51 |
| 2004/0267275 A1 * | 12/2004 | Cournoyer et al. ............. | 606/99 |

FOREIGN PATENT DOCUMENTS

WO 2006116234 A2 11/2006

OTHER PUBLICATIONS

International Search Report for PCT/US08/56814 mailed Aug. 22, 2008.

* cited by examiner

*Primary Examiner* — Eduardo C Robert
*Assistant Examiner* — Nicholas Plionis
(74) *Attorney, Agent, or Firm* — Baker & McKenzie LLP

(57) ABSTRACT

Disclosed embodiments relate to a fixation device for use in supporting and/or aligning an injured body part. An exemplary disclosed fixation device uses a pair of thumb wheel control elements to provide controlled rotational micromovements of a joint fracture. The control elements, their associated drive systems, and at least a tension member allow for converting a rotational force to a translational force to be applied to a driven article in one direction. In addition, the fixation device may incorporate a drive system that introduces a simultaneous longitudinal translation of bone pins with rotation, in order to provide for a translated point of origin of rotation between the fixation device and the affected body part supported by the fixation device.

20 Claims, 12 Drawing Sheets

ADJUSTABLE FIXATION DEVICES INCORPORATING DRIVE SYSTEMS

CROSS-REFERENCE TO RELATED APPLICATIONS

This application claims priority to U.S. Provisional Application No. 60/943,816, filed on Jun. 13, 2007, entitled "DRIVE SYSTEMS AND DEVICES INCORPORATING DRIVE SYSTEMS," which is incorporated herein by reference in its entirety.

FIELD OF THE INVENTION

The disclosed embodiments relate generally to medical device technology, and more specifically to orthopedic fixation devices for treating contracture and to the drive systems that allow precise control for positioning and locking such fixation devices.

BACKGROUND OF THE INVENTION

Oftentimes, injury to a joint or bone can result in fracture or contracture, the latter being an abnormal tightening or shortening of the muscles and/or ligaments that may act to prevent a normal range of motion for the affected body part. Contracture may also be a congenital condition restricting motion. Treatment regimens for fracture and contracture typically involve the use of a fixation device, such as a splint. The splint mechanism would usually be placed on the affected patient by medical personnel in such a way as to align the affected body part during the healing process, holding the affected body part in the proper position for treatment. Since different body parts can have a wide range of motion, there is a need for fixation devices that can initially accommodate a wide range of motions and subsequently maintain the affected body part in one desirable position. Moreover, a typical treatment regimen requires repeated visits to medical professionals so that the fixation device could be periodically adjusted, providing the desired orientation to the affected body part and setting the proper amount of stretching and support for healing. Accordingly, there is also a need for fixation devices that allow for minor adjustments after the fractured body part is substantially maintained in one position.

It is also important that the fixation device support the fractured joint or bone in a way that corresponds to the natural anatomically reduced or aligned position or range of motion for the joint/bone. Conventional fixation devices tend to introduce an unwanted compression to the joint socket or bone gap, since their point of origin for rotation is offset from that of the joint/bone. As the point of rotation is not the same for the affected body part and the fixation device, the body part is forced to absorb the difference, typically by deflecting to compress the gap between bones. This may introduce unwanted stress to the joint/bone that is the target of healing, slowing the healing process and possibly causing additional, unintentional injury.

So, there is a need for an improved fixation device that will allow medical professionals to make effective, calibrated adjustments to the positioning of the injured body part. Additionally, there is a need for a fixation device that provides for a common point of origin for rotation between the fixation device and the injured body part, preventing unintentional injury and speeding healing by ensuring that supported joints/bones are held in a natural alignment position.

BRIEF SUMMARY

Disclosed herein is an adjustable orthopedic fixation device that incorporates a multidirectional drive system. The drive system includes a control element, a drive element, and a coupling mechanism coupling the drive and control elements. The drive system also includes a housing having a base portion extending therefrom and a driven article disposed on the base portion. In one embodiment disclosed herein, the base portion is substantially spherical and the driven article includes a socket-shaped portion that has a substantially spherical inner contour that matches the substantially spherical contour of the base. Generally, the housing provides structural support for the elements of the drive system and is disposed about the drive element. The drive system further includes a plurality of tension members, each having first and second portions. The tension members are preferably positioned orthogonally about the base portion. Moreover, the first portion of each tension member is coupled to the drive element and the second portion of each tension member is coupled to the driven article. The plurality of tension members and the drive element are operable to convert the rotational force applied by the control element to a translational force, which is applied to the driven article in such a way that the driven article is driven in the direction of the translational force.

Several embodiments of the drive element are described and shown herein. In some embodiments, the drive element includes a rotary shaft with a threaded end while the housing includes a threaded bore operable to receive the threaded end. A gear train is used to couple the rotary shaft to the control element, which in some embodiments is a thumb wheel. In other embodiments, the drive element includes a pulley disposed about a shaft extending from a wall of the housing. There are several suitable coupling mechanisms for coupling the pulley to the control element. One such coupling mechanism includes a first sprocket gear associated with the drive element, a second sprocket gear associated with the control element, and a drive chain meshing with the first and second sprocket gears. Alternatively, the coupling mechanism includes a first wheel associated with the drive element, a second wheel associated with the control element, and a drive belt coupling the first and second wheels.

In some embodiments, a gear reduction box is incorporated into the coupling mechanism to substantially maintain the driven article in one orientation. In such embodiments, only a small amount of torque on the control element is required to rotate the driven article (via the drive element), but, in reverse, a large amount of torque on the driven article is required to rotate the control element.

To allow the orthopedic fixation device to have free motion when an adjustment is desired, the fixation device may further include a lever actuator for disengaging the gear reduction box from the coupling mechanism. In some embodiments, a slot is formed in a wall of the housing and the lever actuator is disposed inside the housing. The lever actuator includes a sleeve coupled to a holder having a lever portion that extends through the slot to the outside of the housing. The sleeve connects the coupling mechanism and the gear reduction box together at a first position. When a user moves the sleeve to a second position by moving the lever, the gear reduction box is disengaged from the coupling mechanism, thus allowing the driven article to have free motion.

In addition to a drive system, the adjustable orthopedic device may also include a first portion connected to the driven article, a second portion connected to the housing, and a clamp assembly coupled to the second portion. In some embodiments, the second portion is operable to rotate with respect to the first portion in at least two distinct planes and rotation of the second portion with respect to the first portion occurs simultaneously with longitudinal translation of the clamp assembly along the length of the second portion.

A method is further provided herein for adjustably aligning an injured body part such as a fractured bone with an external fixation device. The method includes providing a fixation device as described herein and includes removably attaching the first and second portions of the external fixation device to first and second bones, respectively. The method further includes translating a first tension member of the plurality of tension members by a fixed amount while simultaneously translating a second tension member of the plurality of tension members by the same fixed amount in an opposite direction in order to rotate the first portion relative to the second portion in a first plane about an origin of rotation. In some embodiments, the method further includes translating a third tension member of the plurality of tension member by a fixed amount while simultaneously translating a fourth tension member of the plurality of tension members by the same fixed amount in an opposite direction in order to rotate the first portion relative to the second portion in a second plane about the origin of rotation. In this embodiment, the second plane is substantially orthogonal to the first plane. The simultaneous translation of opposing tension members in opposite directions allows the tension in the tension members to be maintained, thereby providing a constant compressive force on the driven article against the base portion.

BRIEF DESCRIPTION OF THE DRAWINGS

Embodiments are illustrated by way of example in the accompanying figures, in which like reference numbers indicate similar parts, and in which.

DETAILED DESCRIPTION

Figure 1:
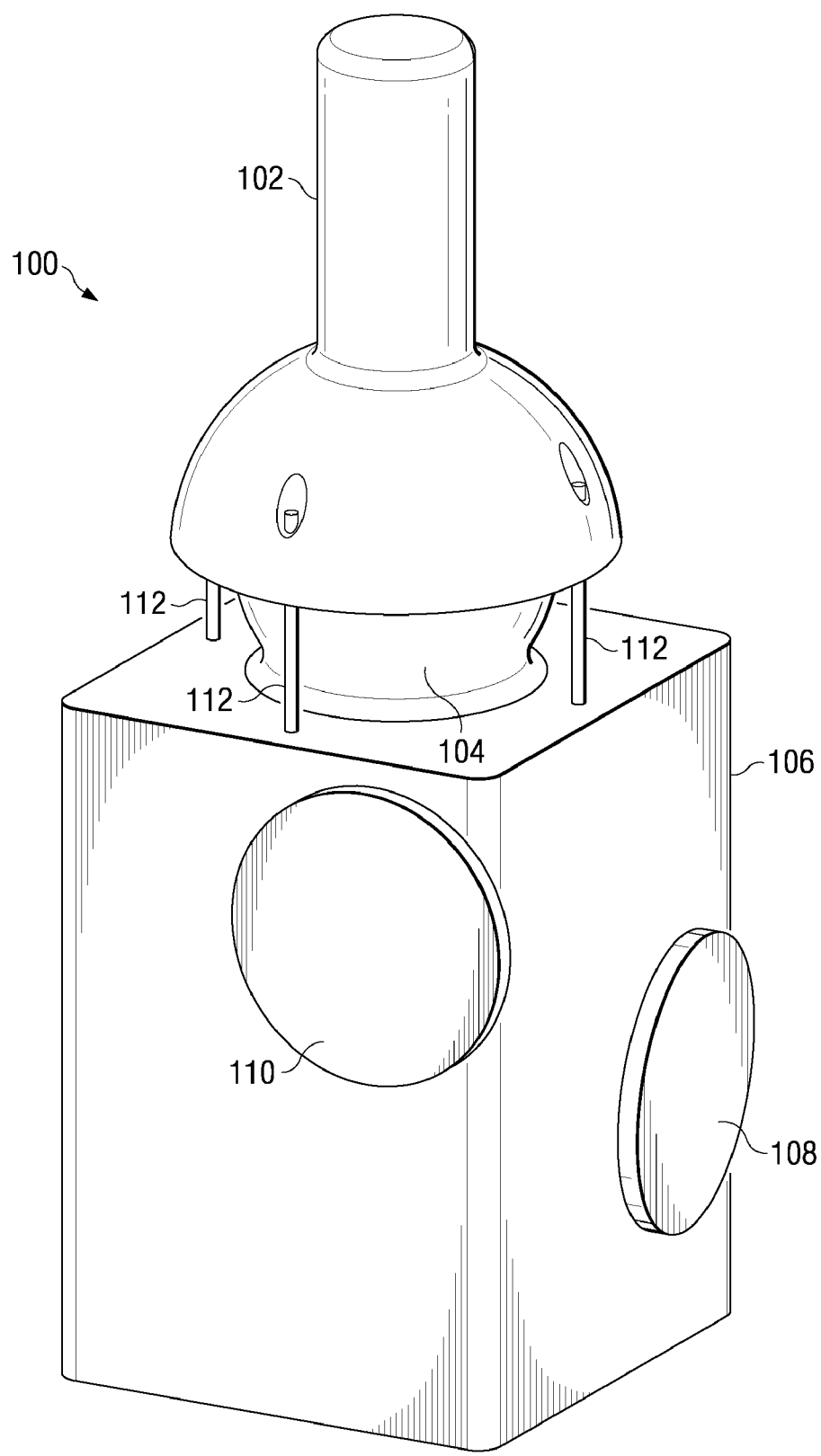
FIG. 1 is a perspective view of an exemplary embodiment of a multi-directional drive system.

The aforementioned need for an improved fixation device can be satisfied using a multi-directional drive system disclosed in this application. FIG. 1 shows an embodiment of a multi-directional drive system 100. The drive system 100 includes a driven article 102 disposed over a base 104, which can either be integrally molded or releasably secured to a housing 106. The base 104 and driven article 102 generally may be configured in any complementary shapes that would allow the driven article 102 to freely rotate about the base 104. In the illustrated embodiment, the base 104 is configured to be substantially spherical while the driven article 102 is configured to have a socket-shaped end so that the base 104 and driven article 102 may resemble a human joint.

The orientation of the driven article 102 relative to the base 104 can be adjusted mechanically in multiple directions by a plurality of tension members 112 that are driven by one or more drive elements (not shown) inside the housing 106 and controlled by control elements 108 and 110. In the embodiment illustrated in FIG. 1, the control elements 108 and 110 each comprise a thumb wheel that is coupled to a drive element inside the housing 106. Although an illustration of the drive elements is not provided in FIG. 1, several exemplary embodiments of the drive elements are illustrated in FIGS. 3-7. It is to be appreciated that these embodiments are merely demonstrative and other designs of the drive elements can be adopted according to the principles disclosed in this application. Turning back to FIG. 1, the drive elements inside the housing 106 are coupled to a plurality of tension members 112 that pass through openings in the housing 106 and connect to the driven article 102. It is to be appreciated that the tension members 112 may be made from a variety of materials. Highly inelastic materials may be preferred to construct the tension members 112 so that tension may be consistently maintained at all times.

Generally, an adjustment to the orientation of the driven article may be effected by turning the control elements 108 and/or 110 and applying rotational forces to the drive elements inside the housing 106. The drive elements and the tension members 112, in turn, cooperate to convert the applied rotational forces to translational forces, which are exerted on different portions of driven article 102 through the tension members 112. As a result, the tension members 112 drive the driven article 102 to a new orientation relative to the base 104.

Figure 2A:
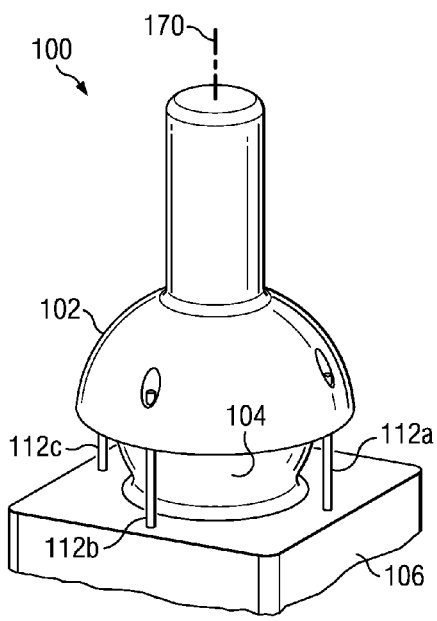
FIG. 2A is a focused view of the upper portion of the multi-directional drive system illustrated in FIG. 1.
Figure 2B:
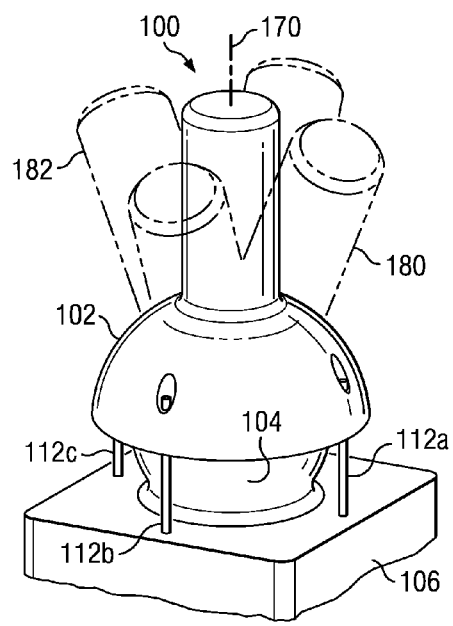
FIG. 2B shows several exemplary orientations of the multi-directional drive system shown in FIG. 2A.
Figure 2C:
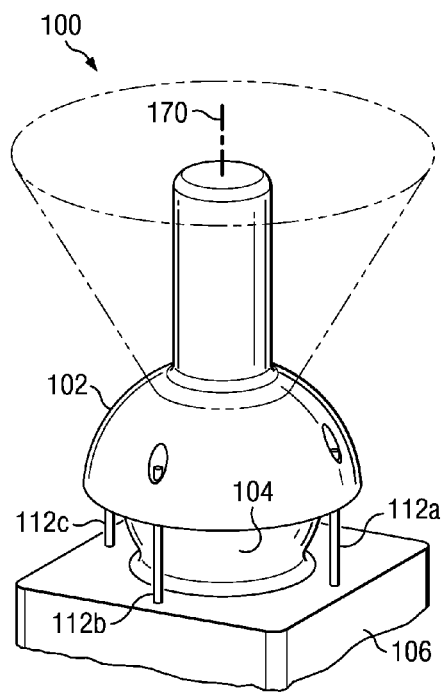
FIG. 2C shows an approximated range of motion of the multi-directional drive system shown in FIG. 2A.

FIGS. 2A, 2B, and 2C illustrate the various orientations of the driven article 102 that can be effected by manipulating the tension members 112. To allow for the maximum range of motion, it is preferred to arrange the tension members 112 orthogonally as illustrated in FIG. 2A. FIG. 2A illustrates two pairs of tension members, 112(a), (c) and 112(b), (d) (not shown in FIG. 2A), being disposed orthogonally about the base 104 and driven article 102. The tension members 112(a) and 112(c) are disposed on opposing sides of the base 104 such that they form a first plane that intersects the axis of rotation 170 of the driven article 102. Tension members 112(b) and 112(d) are similarly disposed on opposing sides of the base 104 such that they form a second plane that intersects the axis of rotation 170 and is orthogonal to the first plane. In applications where it is desirable to limit the range of motion, the tension members 112 may be arranged in other alternative arrangements in accordance with the principles disclosed in this application.

FIG. 2B shows several exemplary orientations of the driven article 102 in the orthogonal first and second planes formed by tension members 112(*a*), (*c*) and 112(*b*), (*d*), respectively. To fix the driven article in one particular orientation, the tensions of the tension members 112(*a*) and 112(*b*) match that of the tension members 112(*c*) and 112(*d*), respectively. To adjust the orientation of the driven article, the tension members may be translated in tandem. To adjust the driven article 102 from position 180 to position 182, for example, tension member 112(*a*) is translated by a fixed amount while tension member 112(*c*) is translated by the same fixed amount in an opposite direction. The tandem translation of the tension members 112(*a*) and (*c*) drives the driven article 102 in the plane formed by the tension members 112(*a*) and (*c*) to position 182. By manipulating the tension members 112(*a*)-(*d*) in pairs, angular motions in two orthogonal planes can be combined to adjust the driven article 102 to any orientation within a complete volume, which is approximated by the conical volume shown in FIG. 2C.

Figure 2D:
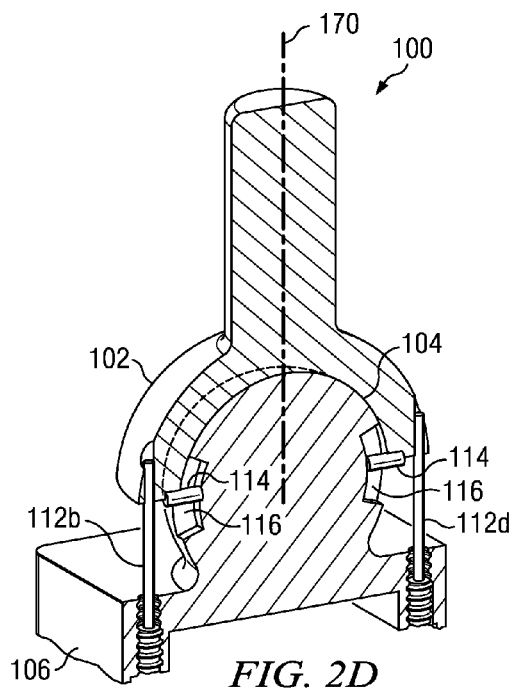
FIG. 2D is a cross-sectional view of the multi-directional drive system shown in FIG. 2A.

One way to make an adjustment requiring angular motions in two orthogonal planes is to sequentially effect angular motion first in a first plane and subsequently in a second plane. A precise adjustment using this method, however, requires the driven article 102 to maintain its coordination in the first plane as it is undergoing angular motion in the second plane. In other words, it is undesirable for the driven article 102 to twist about axis 170 while rotating in the second plane. One way to prevent twisting is to incorporate a guide mechanism that includes a pair of guide pins 114 as illustrated in FIG. 2D. FIG. 2D is a cross-sectional view of the driven article 102 disposed on the base 104, which has grooves 116 formed along opposing peripheral portions of the base 104. The grooves 116 may lie either in the first plane formed by tension members 112(*a*) and (*c*) or in the second plane formed by tension members 112(*b*) and (*d*). The pair of guide pins 114 may either be releasably attached or integrally molded to opposing portions of the driven article 102. The guide pins 114 are received by the corresponding grooves 116, and they are allowed to move along the grooves 116. The coupling of the grooves 116 and guide pins 114 allows the driven article 102 to rotate in the first and second planes but prevents the driven article 102 from rotating and twisting about axis 170.

Figure 3:
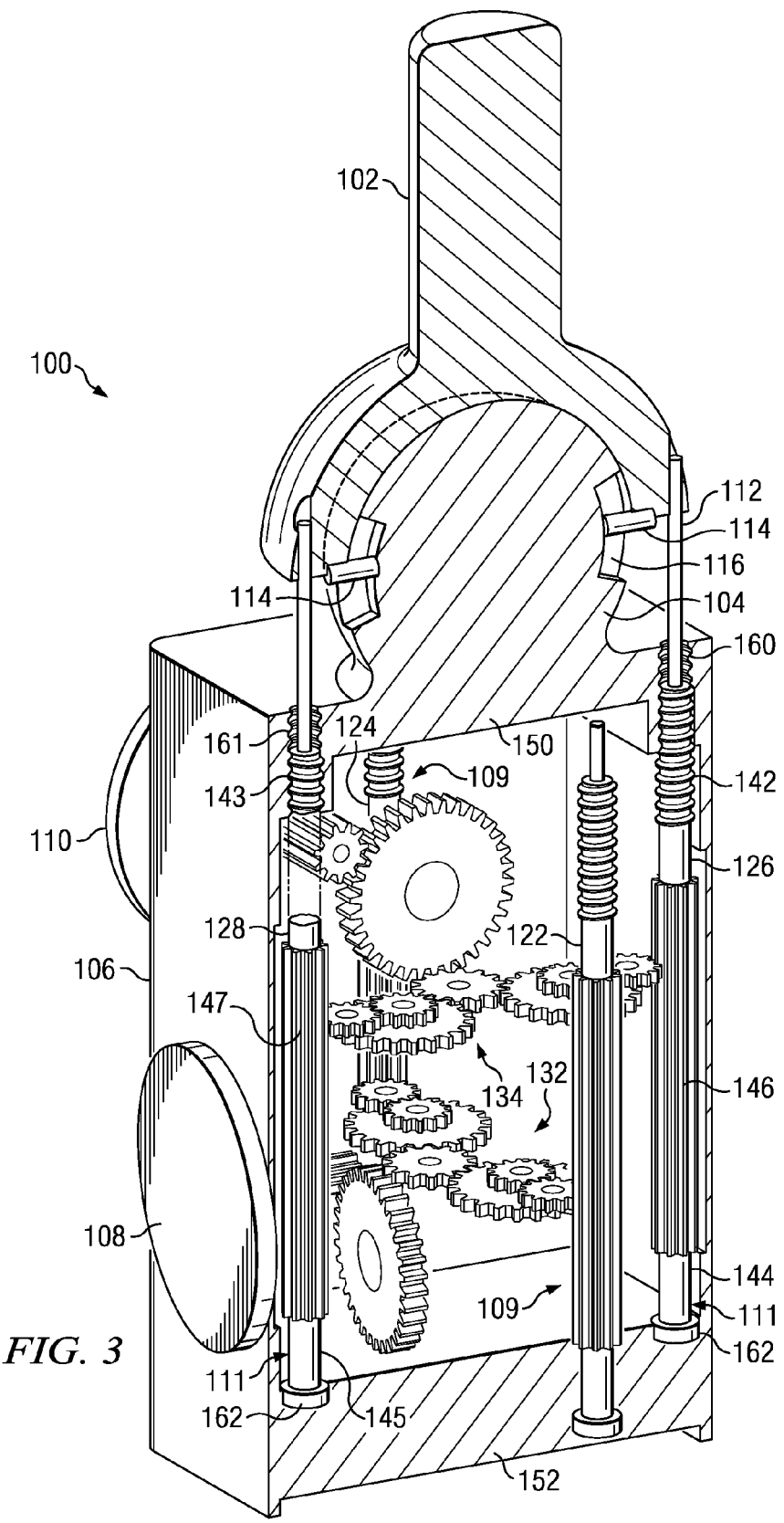
FIG. 3 is a cut-away perspective view of one of the embodiment of the multi-directional drive system shown in FIG. 1.

As discussed previously, the driven article 102 may be driven by translational forces that are converted from rotational forces via the tension elements 112 and the drive elements inside the housing 106. It should be appreciated that the drive elements may take on many different embodiments to allow the drive elements to cooperate with the tension members 112 in converting rotational forces to translational forces. One such embodiment is illustrated in FIG. 3, which provides a cut-away, perspective view of the multi-directional drive system 100 shown in FIG. 1. In this embodiment, a first drive element 109 comprises a pair of drive shafts 122 and 124 that are coupled to the control element 108 by a gear train. 132. In addition to the first drive element 109, a second drive element 111 comprises another pair of drive shafts 126 and 128 that are similarly coupled to the control element 110 by a gear train 134. Drive shaft 126, which is generally representative of the other drive shafts, includes a first end 142 having external threads, an unthreaded second end 144, and a gear-toothed portion 146 between the first and second ends 142 and 144. Drive shaft 128 includes a first end 143 having external threads, an unthreaded second end 145, and a gear-toothed portion 147 between the first end 143 and second end 145. The gear-toothed portion 146 allows the drive shaft 126 to be engaged and rotated by the gear train 134. Moreover, the first and second ends 142 and 144 allow the drive shaft 126 to be disposed longitudinally between a first wall 150 and a second wall 152 of the housing 106. The externally threaded first end 142 is received by an internally threaded bore 160 in the first wall 150 while unthreaded end 144 is received by a bearing 162 located inside a void in the second wall 152. Of course, bore 160 and the opposing bore 161 have opposite threads so that when drive shafts 126 and 128 are rotated in the same direction, they would translate longitudinally in opposite directions. The bearing 162 may be an antifriction element operable to reduce the torsional friction created by the unthreaded end 144 when the drive shaft 126 is rotated. Extending from outside the housing 106, the tension member 112 is disposed through the bore 160 and is coupled either integrally or releasably to drive shaft 126 via the threaded end 142.

It is to be appreciated that the embodiment described in FIG. 3 can be modified according to the principles disclosed in this application. For example, although drive shaft 126 is generally representative of the other drive shafts, specific embodiments of each drive shaft may be varied according to the principles disclosed in this application. In some embodiments, drive shafts 122 and 124 may be configured to have two threaded ends and both walls 150 and 152 may have corresponding threaded bores operable to receive such threaded ends. In other embodiments, one or both of the gear trains 132, 134 may include an additional gear on one portion thereof, thus permitting opposite movement of the corresponding drive shafts. Of course, in such an embodiment, the threads within the bores of the corresponding drives shafts would be aligned in the same direction. In yet another embodiment of the multi-directional drive system, there may be more than two control elements and the housing may be shaped in a variety of ways to adapt and support the additional control elements and the drive elements that are coupled to the control elements.

Figure 4A:
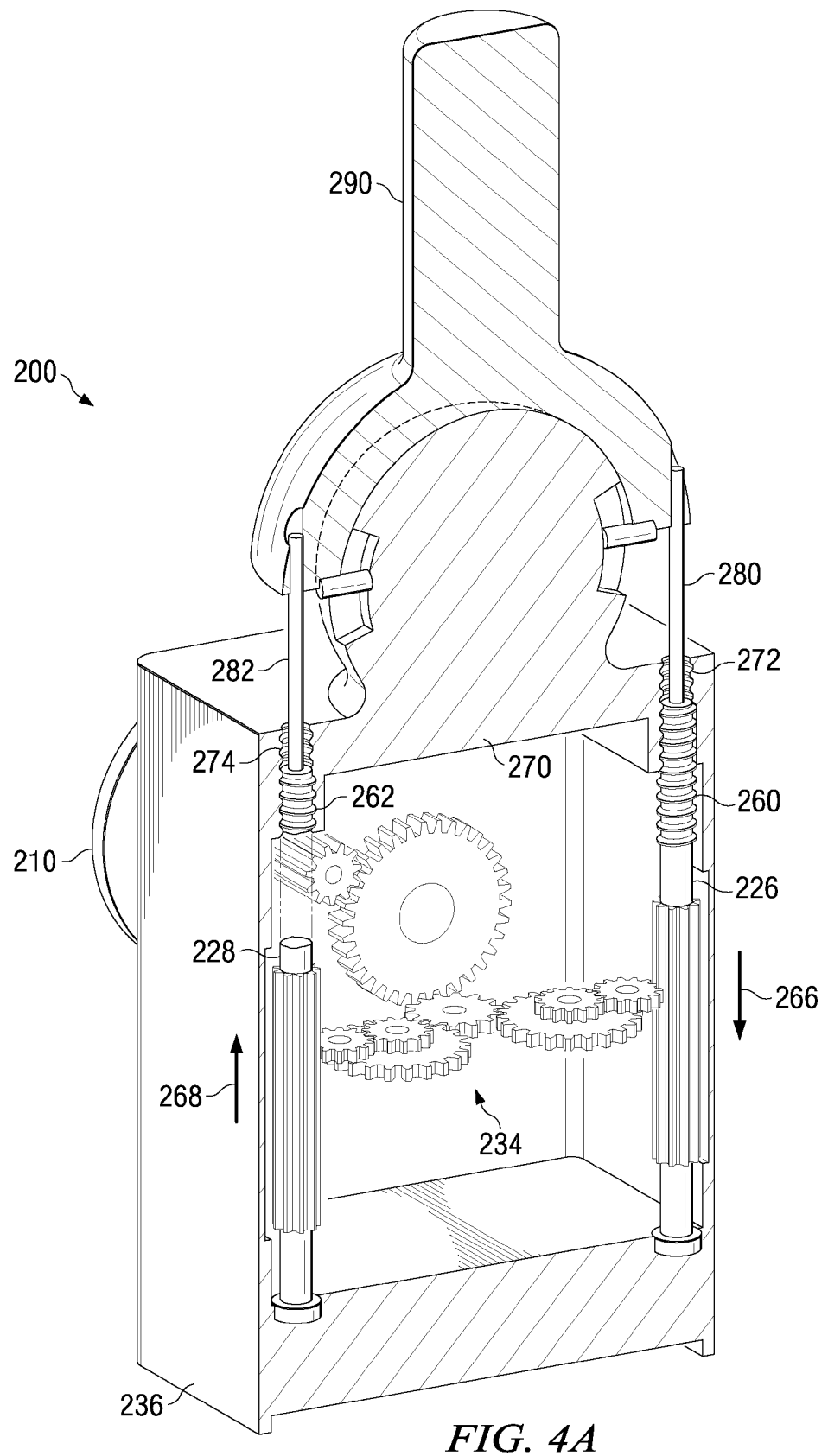
FIG. 4A is a cut-away elevational view of a portion of the multi-directional drive system of FIG. 3.
Figure 4B:
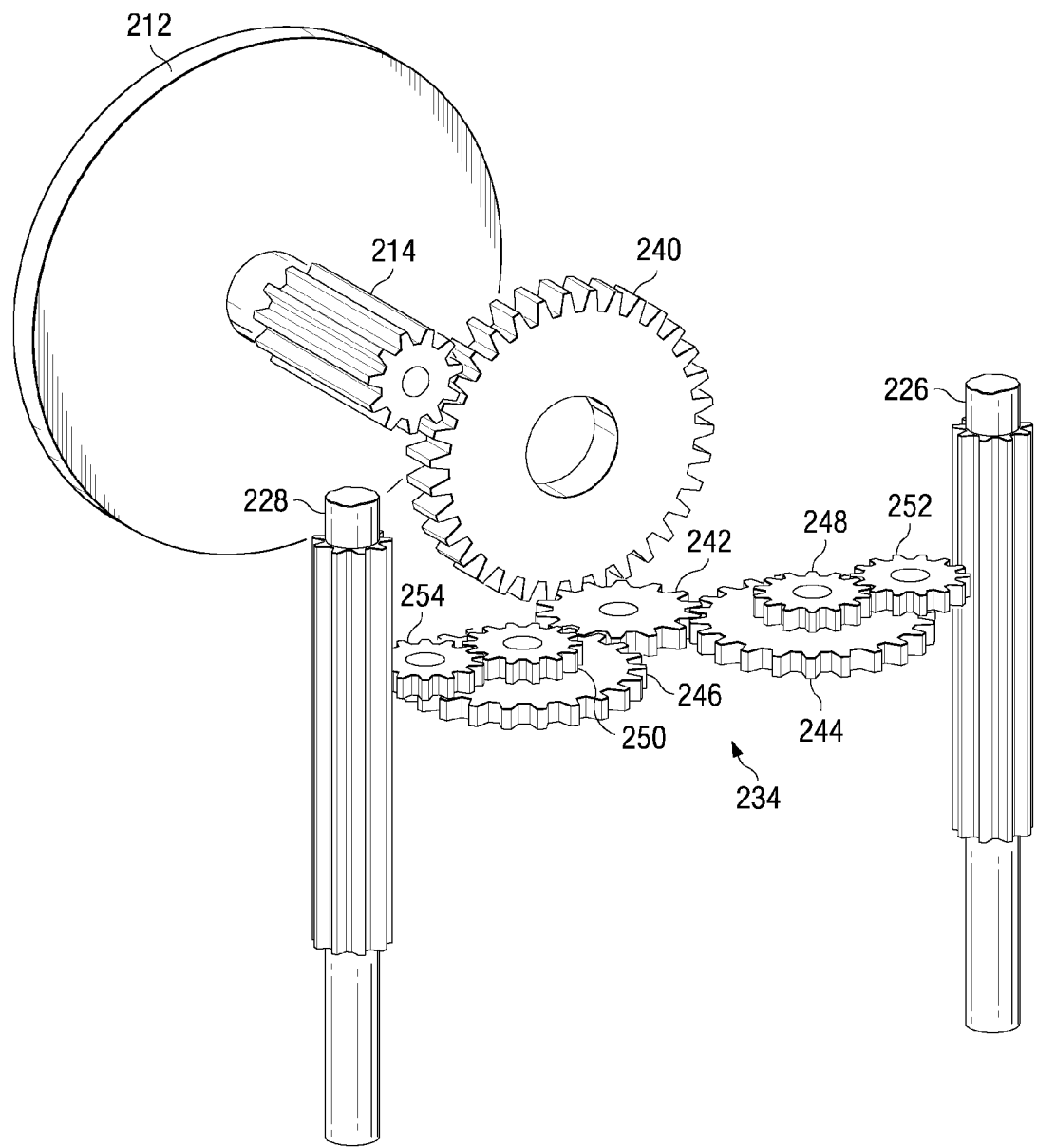
FIG. 4B is a detailed view of an embodiment of the control element, drive element, and coupling mechanism of the multi-directional drive system shown in FIG. 4A.
Figure 4C:
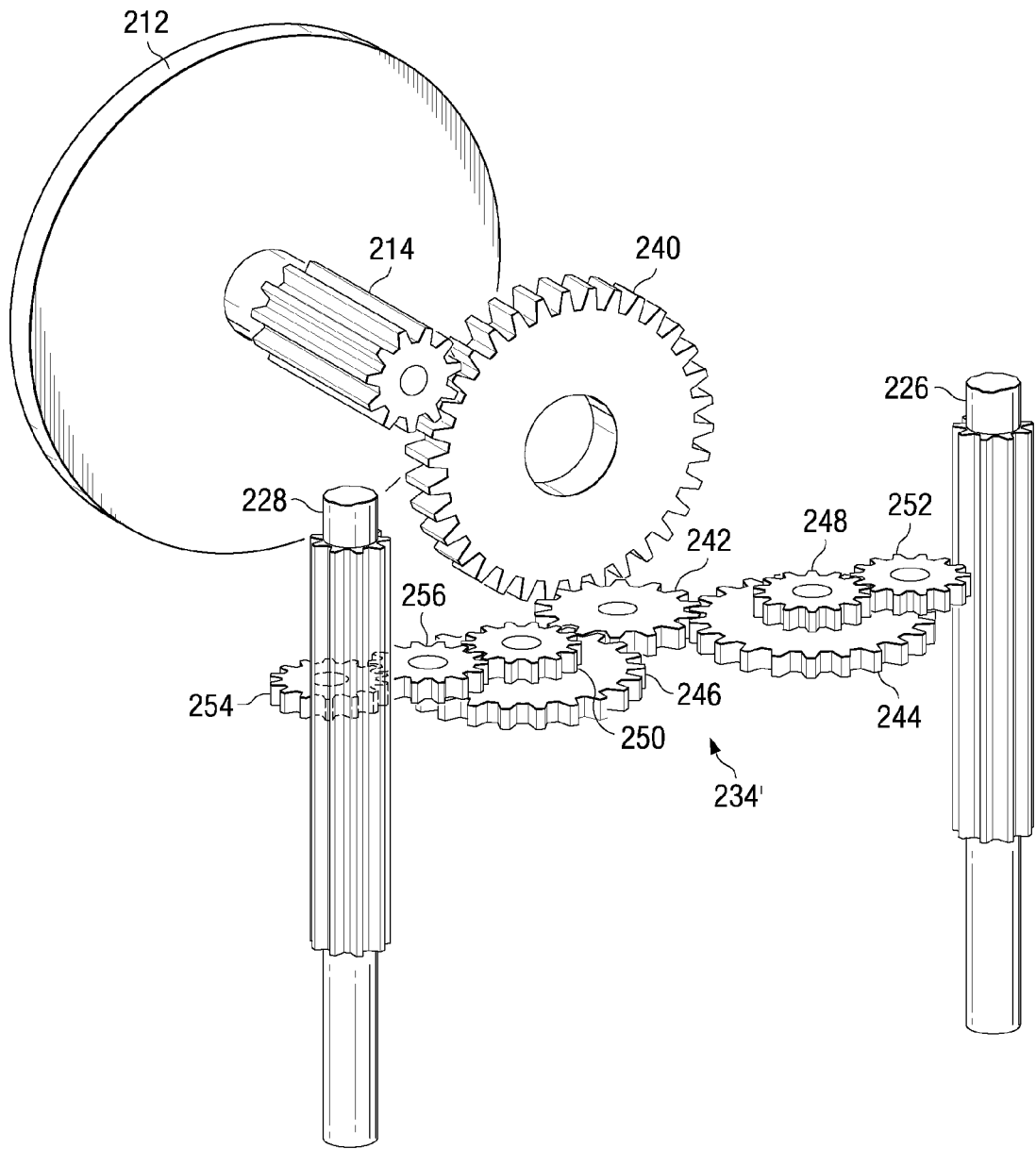
FIG. 4C is a detailed view of another embodiment of the coupling mechanism of the multi-directional drive system shown in FIG. 4A.

Referring to FIGS. 4A, 4B, and 4C, an embodiment of a multi-directional drive system 200 is provided to demonstrate the interoperability of the control element, drive element, and tension members. It should be appreciated that for purpose of explanation, only one gear train is shown in FIGS. 4A-C. However, various embodiments may include one or more gear trains. The drive system 200 shown in FIG. 4A includes a control element 210, a drive element in the form of drive shafts 226 and 228, a gear train 234 coupling the control element 210 and drive shafts 226 and 228, and a housing 236 disposed about the gear train 234. FIG. 4B shows a detailed view of the gear train 234 coupling the control element 210 and drive shafts 226 and 228. Referring to FIG. 4B, the control element 210 includes a wheel 212 and a rotary shaft 214 extending from the wheel 212, wherein the rotary shaft 214 has a gear-toothed portion. The gear train 234 includes: 1) an input gear 240 aligned in a first plane and driven by the rotary shaft 214; 2) a sun gear 242 aligned in a second plane orthogonal to the first plane and driven by the input gear 240; 3) planetary gears 244 and 246 driven by the sun gear 242; 4) moon gears 248 and 250 driven by the shafts of the planetary gears 244 and 246, respectively; and 5) output gears 252 and 254 driven by the moon gears 248 and 250, respectively. The output gears 252 and 254, in turn, drive the drive shafts 226 and 228, respectively. Each gear in the gear train 234 may be disposed about a shaft extending from a wall of the housing 236 or a support plate (not shown) disposed inside the housing 236.

When wheel 212 is rotated, it applies a rotational force that is transferred by the gear train 234 to the drive shafts 226 and 228. Initially, the rotation of wheel 212 causes the rotary shaft 214 to rotate and drive the input gear 240 in the first plane. The rotation of the input gear 240, which may be a spur gear or a bevel gear, causes the sun gear 242 to rotate in the second plane. In the embodiment illustrated in FIG. 4B, the input gear 240 is a spur gear directly driving the sun gear 242. It is to be appreciated that input gear 240 may also be a bevel gear operable to drive an orthogonal bevel gear that shares a common support shaft with the sun gear 242. In this alternative embodiment, rotation of the input gear 240 would drive the orthogonal bevel gear and cause both orthogonal bevel gear and the sun gear 242 to rotate in the same direction.

The rotation of the sun gear 242 consequently triggers the rotation of the planetary gears 244 and 246, the moon gears 248 and 250, and the output gears 252 and 254. Ultimately, the rotation of the output gears 252 and 254 drives the drive shafts 226 and 228 about their longitudinal axis. Because the drive shafts 226 and 228 are coupled to the sun gear 242 by identical gear train arrangement (planetary-moon-output gears), the drive shafts 226 and 228 rotate in the same direction.

Referring back to FIG. 4A, a first end 260 of the drive shaft 226 may be configured to have an external thread, and a first wall 270 of the housing 236 may be configured to have a bore 272 with an internal thread. The external thread of the first end 260 corresponds to the internal thread of bore 272 so as to allow the first end 260 to be received in the bore 272 as illustrated in FIG. 4A. The threaded coupling of the first end 260 with the bore 272 allows the drive shaft 226 to move along its longitudinal axis when is it rotated by the output gear 252. As a result, the rotational force of the shaft 226 is converted to a translational force. If the shaft 226 rotates and moves longitudinally in direction 266 shown in FIG. 4A, it translates the tension member 280 and indirectly applies a translational force to the driven article 290. Translating the tension member 280, however, is not enough to adjust the orientation of the driven article 290. As discussed previously, the opposing tension member 282 may also be translated in tandem to make an adjustment. To achieve this goal, the first end 262 of the drive shaft 228 may be threaded and the first wall 270 of the housing 236 may have another threaded bore 274 defined therein that corresponds to the threaded first end 262. Because the drive shafts 226 and 228 rotate in the same direction, the threads of the first end 262 and bore 274 are reversed from those of the first end 260 and bore 272 so as to allow the drive shaft 228 to move longitudinally in a direction 268 that opposes the direction 266. As the drive shaft 228 moves in direction 268, the tension member 282 may be translated and an adjustment to the orientation of driven article 290 may be effected.

In addition to the reversed thread configuration, opposite movements of the drive shafts 226 and 228 may be effected by modifying the gear train 234. FIG. 4C illustrates a modified gear train 234' that may be incorporated into drive system 200 in FIG. 4A. Gear train 234' is similar to gear train 234 except that gear train 234' has an additional idler gear 256 disposed between the output gear 254 and moon gear 250. The addition of an intermediary idler gear 256 reverses the direction of rotation of the final gear, which is the drive shaft 228. This consequently allows the gear train 234' to rotate drive shafts 226 and 228 in opposing directions, which would cause the drive shafts 226 and 228 to move in opposing longitudinal directions if their first ends 260 and 262 are threaded in the same direction.

Figure 5:
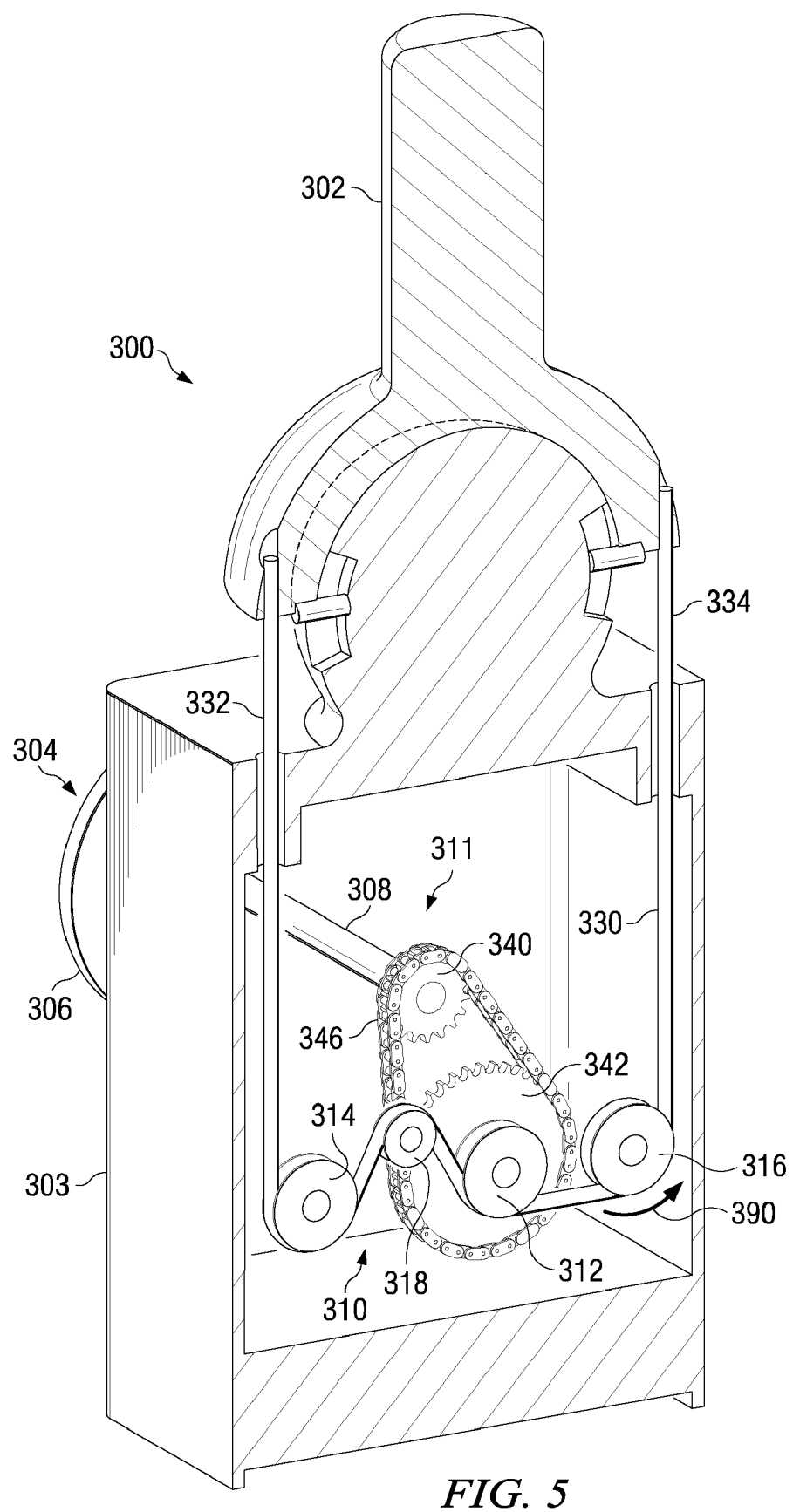
FIG. 5 is a cut-away perspective view of another embodiment of the multi-directional drive system of FIG. 1.

Another embodiment of a drive element 310 is illustrated in FIG. 5, which is a cut-away perspective view of a multi-directional drive system 300. The drive element 310 includes a drive pulley 312, roller pulleys 314 and 316, and tension pulley 318. The pulleys can be made from a variety materials depending on the specific application of the drive system 300. If, for example, the application of drive system 300 requires the pulleys to withstand large tension, the preferred material may be high-density polyethylene or other materials having similar properties.

Interconnecting and engaging each pulley is a linkage element 330, which includes first and second end portions, each extending from the driven article 302 into the housing 303. The first and second end portions are referred to herein as the first and second tension members 332 and 334. The first and second tension members 332 and 334 are coupled to the driven article 302 either releasably or integrally. Beginning from the first tension member 332, the linkage element 330 extends in a substantially vertical plane to the roller pulley 314 and partially wraps around it. From the roller pulley 314, the linkage element 330 extends to and partially wraps around the top portion of the tension pulley 318. The linkage element 330 further extends to the drive pulley 312 and wraps around it substantially. Extending from the drive pulley 312, the linkage element 330 partially wraps around the bottom portion of the roller pulley 316, and extends toward the second tension member 334 in a substantially vertical plane.

Collectively, the pulleys of the drive element 310 cause the first and second tension members 332 and 334 to translate in opposite directions, which imparts motion to the driven article 302. Individually, the drive pulley 312 is operable to translate the linkage element 330 in either direction, which would effect a translation of the first and second tension members 332 and 334. The roller pulleys 314 and 316 are operable to direct the force exerted on the driven article 302 by aligning the first and second tension members 332 and 334 in planes that are substantially vertical. The tension pulley 318 is operable to indiscriminately increase the overall tension of the linkage element 330.

The control element 304 in this embodiment includes a wheel 306 and a rotary shaft 308 extending from the wheel 306. The control element 304 and drive element 310 are coupled by a coupling mechanism 311. In this embodiment, the coupling mechanism 311 includes a first sprocket gear 340 disposed about the rotary shaft 308, a second sprocket gear 342 disposed about a rotary shaft (not shown) that supports the drive pulley 312, and a drive chain 346 meshing with the first and second sprocket gears 340 and 342.

In operation, the wheel 306 is rotated in a first direction, causing the first sprocket gear 340 to also rotate in the first direction. The drive chain 346, in turn, transfers the rotational force to the second sprocket gear 342 and drive pulley 312, causing them to also rotate in the first direction. At this point, the drive element 310 and linkage element 330 cooperate to convert the applied rotational force to a translational force. Wound about the drive pulley 312, the linkage element 330 responds to the rotation of the drive pulley 312 by translating its first and second end portions. If the drive pulley 312 is rotated in direction 390, the first tension member 332 would shorten while the second tension member 334 would lengthen. The shortening of the first tension member 332 thus results in a translational pull force on the driven article 302. In contrast, the lengthening of the second tension member 334 allows the driven article 302 to be pulled by the first tension member 332. If the drive pulley 312 is rotated in the direction opposite to direction 390, the result would be the opposite of that just described.

Figure 6:
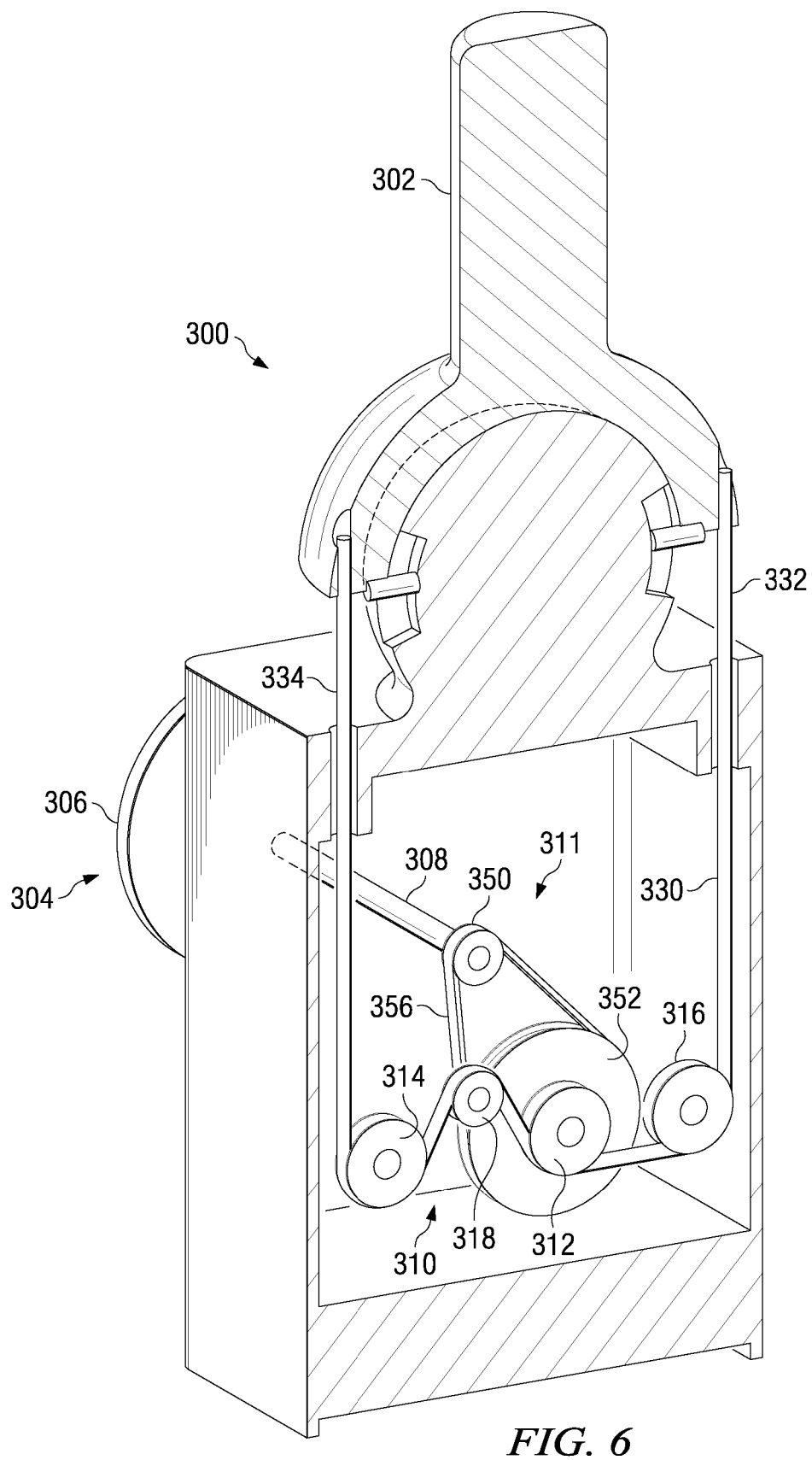
FIG. 6 is a cut-away perspective view of yet another embodiment of the multi-directional drive system shown of FIG. 1.

It is to be appreciated that the exemplary embodiment illustrated in FIG. 5 can be modified according to the principles disclosed. For example, one or more slots may be formed in the housing to allow the shafts (not shown) supporting the roller pulleys 314 and 316 or the tension pulley 318 to move up or down, thus adjusting the overall tension of the drive belt. In an alternative embodiment, the coupling mechanism 311 may include a drive belt 356 and wheels 350 and 352 as illustrated in FIG. 6. In this embodiment, the first wheel 350 is disposed about the rotary shaft 308, a second wheel 352 is disposed about the rotary shaft (not shown) that supports the drive pulley 312, and the drive belt 356 connects the first and second wheels 350 and 352. The drive belt 356 may be tightly tensioned so that rotation of the first wheel 350 effects rotation of the second wheel in the same direction. Additionally, a slot (not shown) may be formed in the housing to permit the control element 304 to move up, thereby increasing the tension of the drive belt.

Figure 7A:
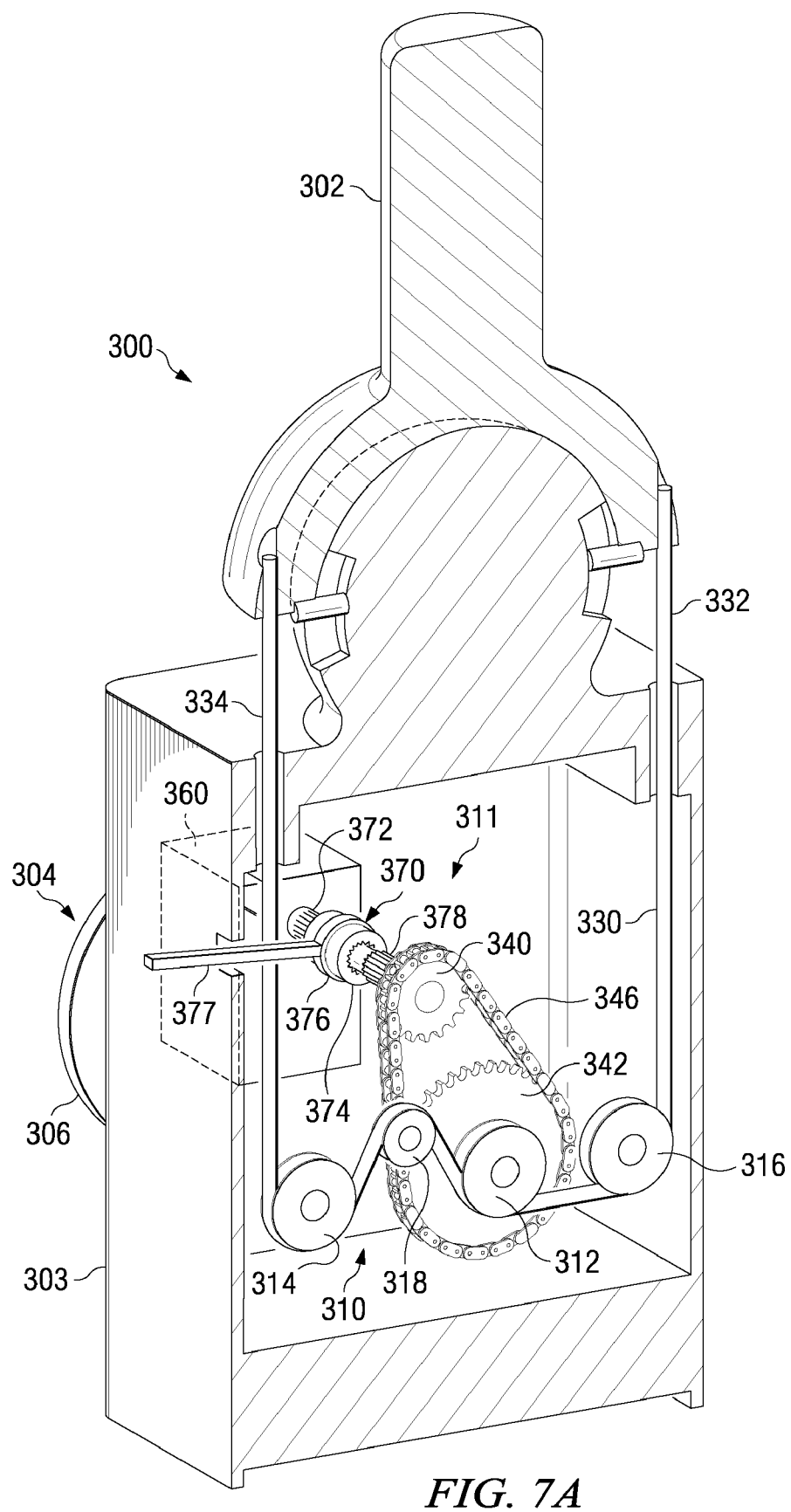
FIG. 7A is a cut-away elevational view of an exemplary embodiment of a multi-directional drive system with a lever actuator and a gear box.

It should be appreciated that the various embodiments of the multidirectional drive system 300 discussed herein may be modified to satisfy the design needs of the final product. For example, the use of a fixation device incorporating the drive system 300 may often subject the driven article 302 to large external torque. Accordingly, there could be a special need to withstand the applied external torque and substantially maintain the orientation of the driven article 302. In this regard, a gear reduction box 360 can be incorporated into the coupling mechanism 311 as illustrated in FIG. 7A to substantially prevent the driven article 302 from changing its orientation. The gear reduction box 360 is connected to shaft 308 of the control element 304 and a first shaft 372 of a lever actuator 370. It is to be appreciated that the lever actuator 370 is an optional element and in some embodiments, the gear reduction box 360 is incorporated without the lever actuator 370, which will be described in more detail below. The gear reduction box 360 may include any gear reduction assembly known in the art that is operable to receive a torque from the drive element and output a reduced torque on the control element. More particularly, gear reduction box 360 is operable to receive a torque input applied by rotation of the shaft 372 and output a substantially minimized torque to the shaft 308. The gear reduction box 360 preferably is also operable to receive a small torque exerted by the control element 304 and output a relatively large torque to the coupling mechanism 311 and drive element 310 so that a user can easily make controlled adjustments to the orientation of the driven article 302. The gear reduction box 360 effectively limits movement of the drive system 300 in one direction. While the orientation of the driven article 302 can be adjusted by a small torque from the control element, when a large torque is applied on the driven article 302, the gear reduction box 360 is able to receive the applied torque and reduce it into a minimal amount so as to prevent the driven article from changing its orientation materially.

Moreover, when an adjustment to the orientation of the driven article is required, it may be desirable to allow the driven article 302 to have free motion. To satisfy this need, the drive system 300 may further include the lever actuator 370 for disengaging the gear reduction box 360 from the coupling mechanism 311. In the embodiment shown in FIG. 7A, a slot is formed in a wall of the housing 303 and the lever actuator 370 includes a sleeve 374 supported by a holder 376 having a lever 377 that extends through the slot to the outside of the housing 303. The inside of the sleeve 374 includes teeth to allow the sleeve 374 to engage the first shaft 372 and a second shaft 378, both of which have mating toothed portions. The first and second shafts 372 and 378 are aligned so that they share the same longitudinal axis, but they are spaced apart as illustrated in FIGS. 7B and C.

Figure 7B:
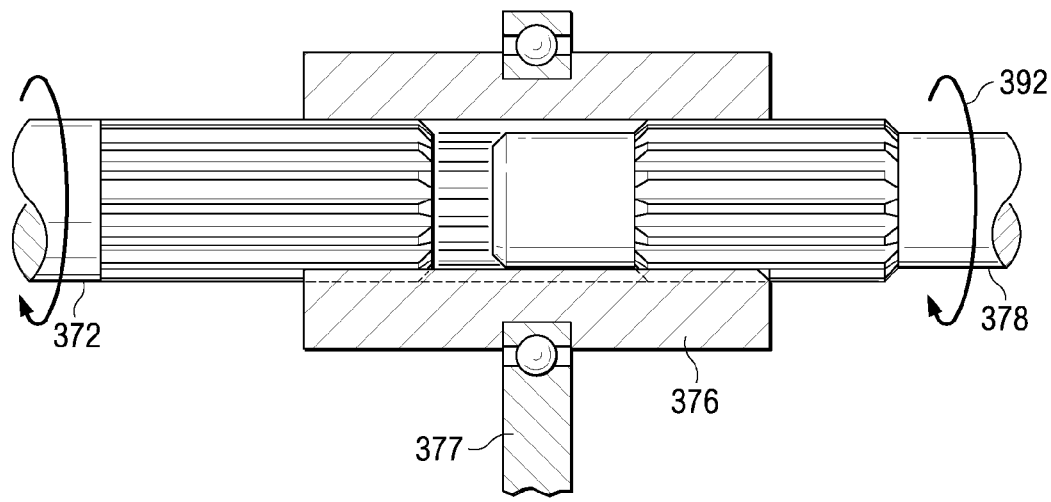
FIG. 7B is a detailed view of the lever actuator in a first position.

FIGS. 7B and C are focused, cut-away views of the sleeve 374 at the engaged and disengaged positions, respectively. At the engaged position as illustrated in FIG. 7B, the internal teeth of sleeve 374 mate with those of the first and second shafts 372 and 378, and this allows the sleeve 374 to function as a connector that connects the first and second shafts 372 and 378. Consequently, rotating one shaft would cause the other shaft to rotate in the same direction. If the first shaft 372 is rotated in direction 392, for example, the second shaft 378 would also rotate in direction 392. Referring back to FIG. 7A, when the first and second shafts 372 and 378 are connected, any torque applied on the driven article 302 would be received by the gear reduction box 360 and reduced to a minimal amount. Accordingly, the orientation of driven article 302 is substantially unchanged.

Figure 7C:
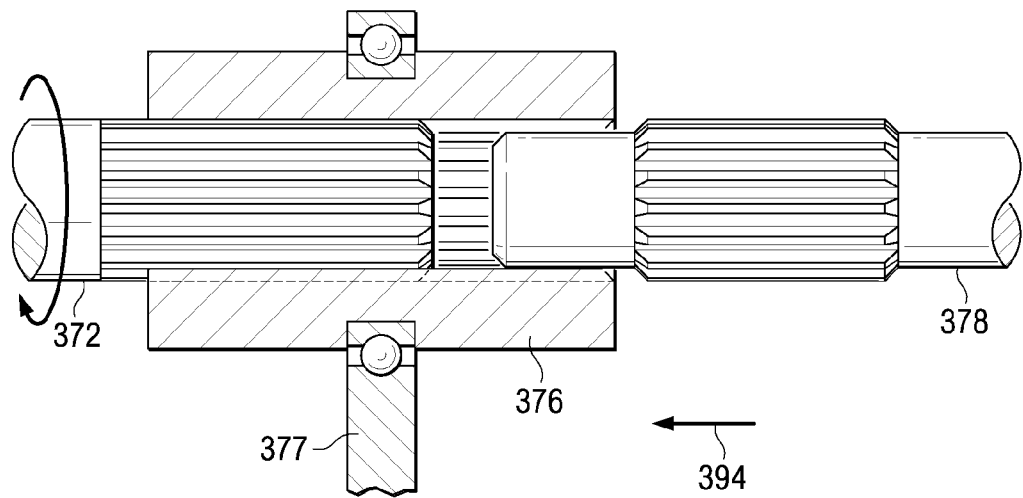
FIG. 7C is a detailed view of the lever actuator in a second position.

Turning to FIG. 7C, when the sleeve 374 is moved to the disengaged position by moving the lever portion 377 in direction 394, the internal teeth of the sleeve 374 are only able to mate with the teeth of shaft 372 but not those of shaft 378. Such configuration means that a rotation of one shaft will not cause the other shaft to rotate. Rotating the first shaft 372 in direction 392, for example, would not rotate the second shaft 378. Referring back again to FIG. 7A, the gear reduction box 360 is disengaged from the coupling mechanism 311 when the first and second shafts 372 and 378 are not connected. Consequently, any torque applied on the driven article 302 would not be received by the gear reduction box 360 and would cause the driven article 302 to freely rotate. It should be appreciated that the lever actuator 370 may be modified and incorporated into any embodiments discussed in the present application according to the principles disclosed herein.

Figure 8:
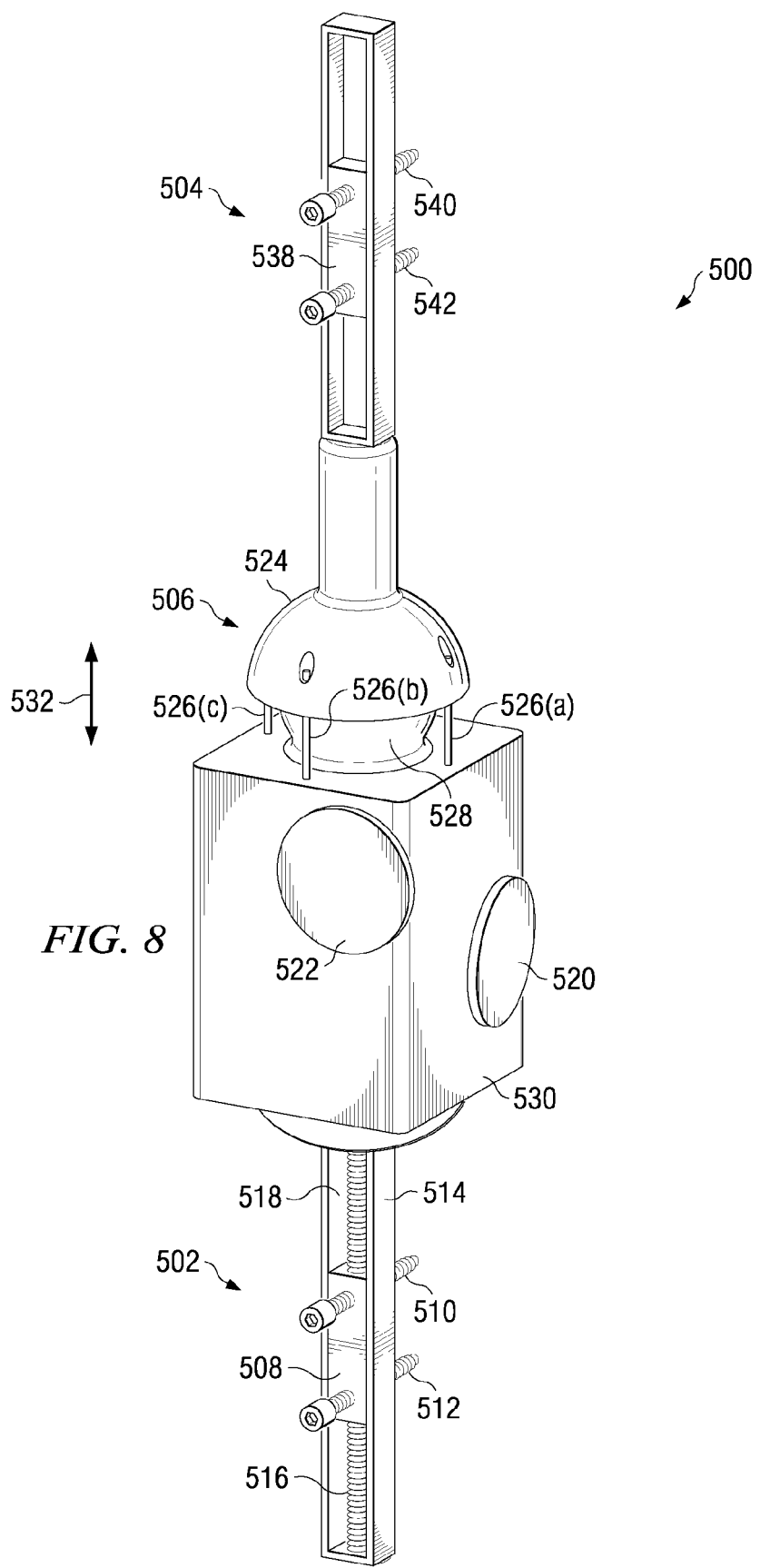
FIG. 8 is a perspective view of a fixation device incorporating a multi-directional drive system.

Turning next to FIG. 8, an external fixation device 500 is shown that incorporates teachings of the present disclosure. For example, the device 500 can be attached to a patient's arm and hand (not shown) for treating a wrist contracture. Such an external fixation device 500 may be used to treat a wide variety of fractures or contractures in skeletal joints, either congenital or acquired. Of course, fixation equipment and methods incorporating teachings of the present disclosure may be used in other orthopedic applications, such as bone lengthening. External fixation device 500 may be satisfactorily used to treat a wide variety of orthopedic indications. A fixation device incorporating teachings of the present disclosure may be formed from a wide variety of materials. For some applications, external fixation device 500 may be formed from aluminum and/or stainless steel or other metal alloys satisfactory for use in treating orthopedic indications. For other applications various components and parts associated with external fixation device 500 may be formed from high strength composite materials and/or cermets.

The particular embodiment of the fixation device 500 shown in FIG. 8 is designed to accomplish two separate but related goals. First, it employs a control-drive system allowing for the type of precise and calibrated movements needed to allow medical professionals to properly orient the fixation device 500 to stretch and/or align an injured body part in the proper orientation for healing. This precise control allows for effective initial orientation of the fixation device 500, as well as simplifying any periodic re-orientation of the fixation device 500 throughout the treatment process. In addition, the disclosed embodiment improves the effectiveness of the fixation device 500 by allowing for natural bone alignment despite the rotation introduced by the fixation device 500. It may translate the point of origin of rotation from the fixation device 500 to the center of rotation of joint fracture, thus preventing any unwanted compression forces upon the bone that could delay healing.

Accordingly, the fixation device 500 disclosed below can be configured to address either or both of these goals, thereby assisting in the healing process. While the embodiment illustrated in FIG. 8 is designed to accomplish both goals simultaneously, those skilled in the art will understand that the fixation device may be configured to accomplish either of these purposes alone as well. Furthermore, persons skilled in the art will recognize that FIG. 8 discloses only an exemplary embodiment of such a fixation device. These and all other equivalent embodiments are intended to be included within the scope of the disclosure.

In the disclosed embodiment of FIG. 8, external fixation device 500 includes a first portion 502 and a second portion 504 connected by an adjustable joint 506. For example, various embodiments of drive systems 100, 200, and 300 described herein may be integrated into the adjustable joint 506. The adjustable joint 506 can thus be used to position the first portion 502 relative to the second portion 504 as desired. For example, the first portion 502 can be rotated as desired relative to the second portion 504.

The first portion 502 includes a clamp assembly 508 for securing a pair of bone screws 510 and 512. The second portion 504 also includes a clamp assembly 538 for securing a pair of bone screws 540 and 542. The first portion 502 also includes a housing 514 having a generally elongated rectangular configuration. A drive screw 516 is disposed within the housing 514. In some embodiments, the second portion 504 can also be provided with a housing and drive screw (not shown) substantially the same as those provided for the first portion or substantially different depending on the application.

The housing 514 includes an elongated slot or opening 518. The drive screw 516 can be rotatably disposed within the elongated slot 518. Threads are formed on the exterior of the drive screw 516 and engaged with the clamp assembly 508 whereby rotation of the drive screw 516 will result in longitudinal movement of the clamp assembly 508 relative to the adjustable joint 506 and the second portion 504.

The adjustable joint 506 rotatably connects the first and second portions 502 and 504. In the embodiment shown in FIG. 8, the adjustable joint 506 allows for controlled rotation of the first portion 502 in the planes defined by tension members 526(a), (c) and 526(b), (d) (not shown).

As discussed previously, any of the drive systems disclosed in this application may be integrated into an adjustable joint 506 for providing desired controlled rotation or articulation of the first portion 502 relative to the second portion 504. The illustrated adjustable joint 506 includes control elements 520 and 522, a driven article 524, tension members 526, a base 528, a housing 530, and drive elements (not shown) inside the housing 530. The first portion 502 is attached to a wall of the housing 530 while the second portion 504 is attached to the driven article 524.

Controlled positioning of the elements of the fixation device 500 requires adjusting the orientation of the driven article 524 relative to the base 528. This task initially involves turning the control elements 520 and 522 to apply rotational forces to the drive elements coupled to the corresponding control elements. The drive elements cooperate with the tension members 526 to convert the applied rotational forces to translational forces in orthogonal planes. The translational forces are then exerted on the driven article 524, causing it to rotate about the base 528.

It may also be beneficial to structure the fixation device 500 so that a rotational axis is maintained at the center of rotation at the bone. Generally, this would be accomplished by providing for simultaneous longitudinal translation accompanying any rotation, in order to ensure that no compression forces are inadvertently introduced to the injured body part. By way of example, the drive system that is adopted so that the adjustable joint 506 can also be used to rotate a drive screw 516 (in addition to orienting the second portion 504 of the fixation device 500 with respect to the first portion 502), resulting in longitudinal translation of the clamp assembly 508 and the bone screws 510 and 512 as indicated by arrows 532. In other words, turning the control elements 520 and 522 can result in simultaneous rotation of the first portion 502 and translation of the clamp assembly 508 and bone screws 510 and 512. Accordingly, the external fixation device 500 generally utilizes the motion between the first portion 502 and the second portion 504 to rotate the drive screw 516. In this regard, rotation of the drive screw 516 may be considered an indirect result of turning the control elements 520 and 522.

Figure 9A:
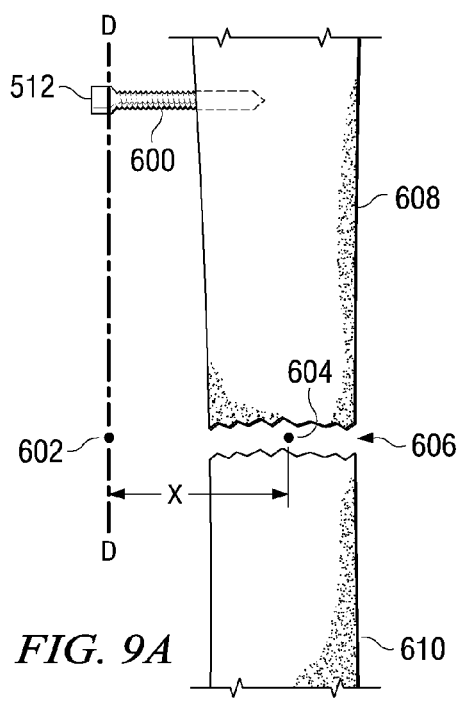
FIG. 9A is a schematic illustration of an adjustable fixation device in a first orientation.

The simultaneous rotation of the first portion 502 and translation of the bone screws 510 and 512 is preferable for reasons described with reference to FIGS. 9A-C. Referring first to FIG. 9A, an axis D-D is shown that represents a longitudinal axis of the first portion 502 (FIG. 7). A bone screw 600 is shown for fixing the first portion 502 of the fixation device 500 (not shown in FIGS. 8A-8C) to a first bone 608. A first origin of rotation point 602 represents a point about which the fixation device 500 rotates when the joint 506 is controlled for rotating the first portion 502 in the plane defined by the axis of first portion 502 and the bone. An origin of rotation point 604 represents the natural origin of rotation for a fracture 606 between the first bone 608 and a second bone 610. Note that the first and second origin points 602 and 604 are offset by a fixed distance X, which remains fixed for each of the FIGS. 9A-C.

Figure 9B:
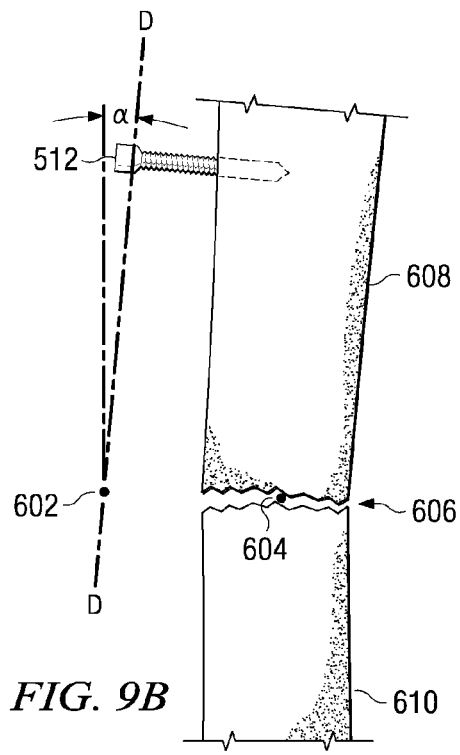
FIG. 9B is a schematic illustration of the adjustable fixation device being adjusted to a second orientation.

FIG. 9B shows the results of the adjustable joint 506 rotating the first portion 502 by an angle α about the first point 602 in the generally horizontal plane. In this case, the distance between the point 602 and the bone screw 512 remained fixed while the first portion 502 was rotated. As a result, rotation about the point 602 of the adjustable joint 506 causes compression of the bone gap at the joint 606.

Figure 9C:
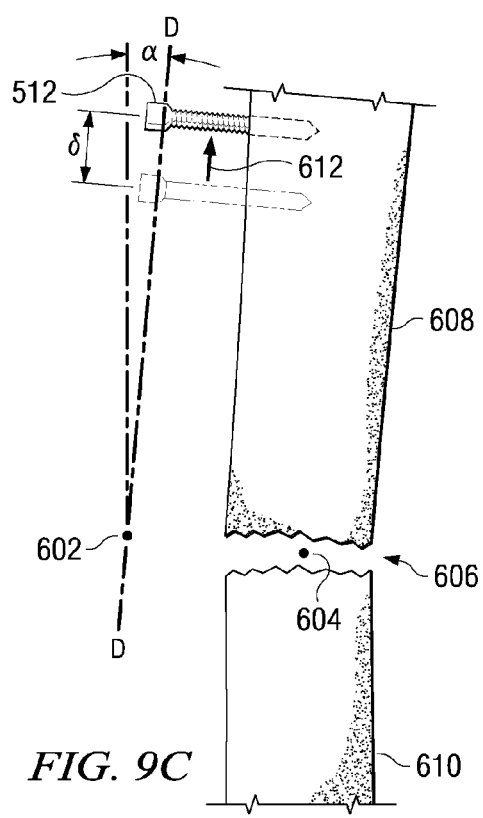
FIG. 9C is a schematic illustration of the adjustable fixation device in the second orientation.

FIG. 9C, on the other hand, shows the results of rotating the first portion 502 in the same manner as it is rotated in FIG. 9B except that the bone screw is translated in the direction indicated by arrow 612 by a distance δ. In other words, while the first portion 502 was rotating by the angle α, the bone screw 512 was translating such that the distance between the point 602 and the bone screw 512 increased by the distance δ. Translating the bone screw 512 while the first portion 502 is rotating effectively transfers the origin of rotation to point 604 so that the rotation of the bone 608 can be maintained about the natural origin of rotation for the joint 606. Preferably the amount of translation δ of the bone screw 512 is determined based on the following relationship:

$$\delta = X \cos(\alpha) \qquad \text{Equation (1)}$$

Thus, the desired amount of translation δ can be determined based on a function of the amount of rotation α of the adjustable joint 506 and the offset X between the first and second origin of rotation points 602 and 604.

Turning back to FIG. 8, the drive system that is adopted to be the adjustable joint 506 can be coupled with the drive screw 516, for example via a gear system (not shown), so that the drive screw 516 rotates as the control elements are rotated. This allows for longitudinal translation of the clamp assembly 508, and thus of the bone screws 510 and 512, as the first portion 502 is rotated. Preferably the drive screw 516 is set to rotate such that the clamp assembly 508 moves according to equation (1) shown above, where X is the distance between the origin of rotation of the adjustable joint 506 and the natural origin of rotation of a joint (e.g., joint 606) and $\alpha$ is the angle by which the first portion 502 is rotated relative to the second portion 504.

Thus, turning the control elements 520 and 522 can result in simultaneous rotation of the first portion 502 and translation of the clamp assembly 508 and bone screws 510 and 512 such that a joint 606 is rotated about its natural origin of rotation 604. So in the exemplary embodiment of FIG. 8, a single fixation device 500 incorporates a fine control-drive mechanism which provides for simultaneous translation while introducing rotation (ensuring proper alignment and natural support for the injured body part). While the drive system that is adopted to be the adjustable joint 506 and the use of simultaneous translation in conjunction with rotation of the fixation device 500 may be used separately, it is particularly beneficial to combine both of these elements into a single device.

While various embodiments in accordance with the principles disclosed herein have been described above, it should be understood that they have been presented by way of example only, and are not limiting. For example, control elements other than a thumb wheel and drive elements other than a drive wheel are contemplated. Thus, the breadth and scope of the invention(s) should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

What is claimed is:

1. An adjustable orthopedic fixation device comprising:
    a control element;
    a drive element coupled to the control element via a coupling mechanism such that rotation of the control element results in rotation of the drive element;
    a housing disposed about the drive element, the housing having a base portion extending therefrom;
    a driven article disposed on the base portion; and
    a plurality of tension members positioned about the base portion and connecting the drive element and the driven article, whereby rotation of the drive element results in translation of more than one of the plurality of tension members in a fixed amount in opposite directions.

2. The adjustable orthopedic fixation device as in claim 1, wherein the base portion is substantially spherical and the driven article includes a socket-shaped portion, the socket-shaped portion having a substantially spherical inner contour that matches a substantially spherical contour of the base.

3. The adjustable orthopedic fixation device as in claim 1, wherein the drive element comprises a rotary shaft having a threaded end, and wherein the housing includes a threaded bore formed therein, the bore being operable to receive the threaded end.

4. The adjustable orthopedic fixation device as in claim 3, wherein the rotary shaft is coupled to the control element by a gear train.

5. The adjustable orthopedic fixation device as in claim 3, wherein a first end of each tension member is coupled to the driven article and a second end of each tension member is coupled to the threaded end.

6. The adjustable orthopedic fixation device as in claim 3, wherein the control element is operable to rotate the rotary shaft about a first axis.

7. The adjustable orthopedic fixation device as in claim 1, wherein the drive element comprises at least one pulley disposed about a support shaft extending from a wall of the housing.

8. The adjustable orthopedic fixation device as in claim 7, wherein the at least one pulley comprises a plurality of pulleys.

9. The adjustable orthopedic fixation device as in claim 7, wherein the coupling mechanism comprises a first sprocket gear associated with the drive element, a second sprocket gear associated with the control element, and a drive chain meshing with the first and second sprocket gears.

10. The adjustable orthopedic fixation device as in claim 7, wherein the coupling mechanism comprises a first wheel associated with the drive element, a second wheel associated with the control element, and a drive belt coupling the first and second wheels.

11. The adjustable orthopedic fixation device as in claim 7, wherein each tension member is an end portion of a linkage element, the linkage element being coupled to the at least one pulley.

12. The adjustable orthopedic fixation device as in claim 1, wherein the coupling mechanism comprises a gear reduction box operable to receive a torque from the drive element and output a reduced torque on the control element.

13. The adjustable orthopedic fixation device as in claim 12, further comprising a lever actuator operable to disengage the gear reduction box from the coupling mechanism.

14. The adjustable orthopedic fixation device as in claim 13, wherein a slot is formed in a wall of the housing and the lever actuator comprises
    first and second shafts, the shafts being spaced apart and each having a toothed portion;
    a sleeve operable to connect the first and second shafts, the sleeve having internal teeth that are operable to mate with the teeth of the first and second shafts; and
    a holder supporting the sleeve, wherein the holder has a lever portion, the lever portion extending from the holder through the slot to outside of the housing.

15. The adjustable orthopedic fixation device as in claim 14, wherein when the gear reduction box is disengaged from the coupling mechanism, the internal teeth of the sleeve mate with the teeth of the first shaft but not with the teeth of the second shaft.

16. The adjustable orthopedic fixation device as in claim 1, further comprising a guide mechanism operable to limit rotational movement of the driven article.

17. The adjustable orthopedic fixation device as in claim 16, wherein the plurality of tension members are positioned orthogonally about the base portion, and further wherein the guide mechanism comprises a groove formed in the base portion operable to receive a pin, the pin being connected to the driven article, whereby the pin allows the driven article to rotate only in orthogonal planes defined by the plurality of tension members.

18. An adjustable orthopedic fixation device comprising:
 a control element;
 a drive element coupled to the control element via a coupling mechanism such that rotation of the control element results in rotation of the drive element;
 a housing disposed about the drive element, the housing having a base portion extending therefrom;
 a driven article disposed on the base portion;
 a plurality of tension member members positioned about the base portion and connecting the drive element and the driven article, whereby rotation of the drive element results in translation of more than one of the plurality of tension members in a fixed amount in opposite directions;
 a first portion connected to the driven article;
 a second portion connected to the housing;
 a first clamp assembly coupled to the first portion; and
 a second clamp assembly coupled to the second portion;
 wherein the first portion is operable to rotate with respect to the second portion in at least two distinct planes; and
 wherein rotation of the first portion with respect to the second portion occurs simultaneously with longitudinal translation of the first clamp assembly along the length of the first portion.

19. The adjustable orthopedic fixation device as in claim 18, wherein the first clamp assembly comprises one or more bone screws allowing the first portion to be releasably attached to a bone at a fixed distance from the bone; and wherein the amount of longitudinal translation of the first clamp assembly approximates the product of the fixed distance between the first portion and the bone and the cosine of an amount of rotation of the first portion with respect to the second portion.

20. The adjustable orthopedic fixation device as in claim 19, wherein the second clamp assembly comprises one or more bone screws allowing the second portion to be releasably attached to a second bone at a fixed distance from the second bone, wherein rotation of the first portion with respect to the second portion occurs simultaneously with longitudinal translation of the second clamp assembly along the length of the second portion.

* * * * *